(12) United States Patent
Cosmescu (10) Patent No.: US 7,935,109 B2
(45) Date of Patent: *May 3, 2011

(54) MULTIFUNCTIONAL TELESCOPIC MONOPOLAR/BIPOLAR SURGICAL DEVICE AND METHOD THEREOF

(76) Inventor: Ioan Cosmescu, Phoenix, AZ (US)

( * ) Notice: Subject to any disclaimer, the term of this patent is extended or adjusted under 35 U.S.C. 154(b) by 981 days.

This patent is subject to a terminal disclaimer.

(21) Appl. No.: 11/465,197

(22) Filed: Aug. 17, 2006

(65) Prior Publication Data

US 2006/0276783 A1  Dec. 7, 2006

Related U.S. Application Data

(63) Continuation of application No. 10/796,748, filed on Mar. 8, 2004, now Pat. No. 7,112,199, which is a continuation-in-part of application No. 09/977,408, filed on Oct. 15, 2001, now Pat. No. 6,702,812, which is a continuation of application No. 09/088,386, filed on Jun. 1, 1998, now Pat. No. 6,355,034, which is a continuation of application No. 08/717,494, filed on Sep. 20, 1996, now abandoned.

(51) Int. Cl.
*A61B 18/18* (2006.01)
(52) U.S. Cl. ............... 606/41; 606/46; 606/48; 606/50
(58) Field of Classification Search .............. 606/41, 606/45–50; 604/21, 22, 30, 35, 113, 114
See application file for complete search history.

(56) References Cited

U.S. PATENT DOCUMENTS

| | | |
|---|---|---|
| 1,731,069 A | 10/1929 | Herman |
| 1,741,461 A | 12/1929 | Herman |
| 3,902,494 A | 9/1975 | Haberlen et al. |
| 3,906,955 A | 9/1975 | Roberts |
| 3,909,586 A | 9/1975 | Landis et al. |
| 4,057,705 A | 11/1977 | Cockrum et al. |
| 4,496,823 A | 1/1985 | Mann |
| 4,545,375 A * | 10/1985 | Cline ........................... 606/42 |
| 4,719,914 A | 1/1988 | Johnson |
| 4,727,238 A | 2/1988 | Mann |
| 4,911,159 A | 3/1990 | Johnson et al. |
| 5,186,714 A | 2/1993 | Boudreault et al. |
| 5,195,958 A | 3/1993 | Phillips |
| 5,234,428 A | 8/1993 | Kaufman |
| 5,234,429 A | 8/1993 | Goldhaber |
| 5,273,524 A | 12/1993 | Fox et al. |

(Continued)

FOREIGN PATENT DOCUMENTS

CN  2159200 Y  3/1994

(Continued)

*Primary Examiner* — Roy D Gibson
(74) *Attorney, Agent, or Firm* — Zeman-Mullen & Ford, LLP (57) ABSTRACT

A multifunctional telescopic monopolar/bipolar electrosurgery pencil is disclosed for use with an electrosurgery unit (ESU). The monopolar/bipolar electrosurgery pencil includes a bipolar electrode having an insulator sandwiched between an active electrode and a return electrode wherein the bipolar electrode is connected to a handpiece capable of alternately effectuating cutting and coagulation with the bipolar electrode. The monopolar/bipolar electrosurgery pencil is capable of functioning as both a monopolar and bipolar device and can be used for open and closed laparoscopic and endoscopic procedures. Telescopic means for adjusting the length of the bipolar electrode is also provided as are means for smoke evacuation and suction/irrigation. The multifunctional telescopic monopolar/bipolar device can also be adapted for use with an ESU argon beam coagulator.

10 Claims, 7 Drawing Sheets

U.S. PATENT DOCUMENTS

| | | | | |
|---|---|---|---|---|
| 5,281,216 A | * | 1/1994 | Klicek | 606/42 |
| 5,318,565 A | * | 6/1994 | Kuriloff et al. | 606/49 |
| 5,451,222 A | | 9/1995 | De Maagd et al. | |
| 5,460,602 A | | 10/1995 | Shapira | |
| 5,472,442 A | | 12/1995 | Klicek | |
| 5,486,161 A | | 1/1996 | Lax et al. | |
| 5,505,710 A | | 4/1996 | Dorsey, III | |
| 5,609,573 A | | 3/1997 | Sandock | |
| 5,626,577 A | | 5/1997 | Harris | |
| 5,662,647 A | | 9/1997 | Crow et al. | |
| 5,693,044 A | | 12/1997 | Cosmescu | |
| 5,814,044 A | | 9/1998 | Hooven | |
| 5,861,002 A | | 1/1999 | Desai | |
| 6,361,532 B1 | * | 3/2002 | Burek | 606/45 |
| 6,702,812 B2 | | 3/2004 | Cosmescu | |
| 6,730,081 B1 | | 5/2004 | Desai | |
| 2001/0018586 A1 | | 8/2001 | Cosmescu | |
| 2002/0058938 A1 | | 5/2002 | Cosmescu | |
| 2005/0113825 A1 | | 5/2005 | Cosmescu | |

FOREIGN PATENT DOCUMENTS

| | | | |
|---|---|---|---|
| EP | 0 502 421 A2 | 2/1992 | |

* cited by examiner

MULTIFUNCTIONAL TELESCOPIC MONOPOLAR/BIPOLAR SURGICAL DEVICE AND METHOD THEREOF

CROSS REFERENCE TO RELATED APPLICATIONS

This application is a continuation of and claims benefit of priority to U.S. Nonprovisional patent application Ser. No. 10/796,748 filed Mar. 8, 2004, now U.S. Pat. No. 7,112,199, which is a continuation-in-part of patent application Ser. No. 09/977,408 filed Oct. 15, 2001, now U.S. Pat. No. 6,702,812, which was a continuation of patent application Ser. No. 09/088,386 filed Jun. 1, 1998, now U.S. Pat. No. 6,355,034, which was a continuation of patent application Ser. No. 08/717,494 filed Sep. 20, 1996, now abandoned, which applications are hereby incorporated by reference in their entirety.

FIELD OF INVENTION

The present invention relates generally to an electrosurgical unit (ESU) pencil. More specifically, the present invention relates to an ESU pencil having a bipolar electrode wherein the active and return electrode are contained within the same tip of the ESU pencil and are separated by a high temperature resistant radio frequency (RF) dielectric. The ESU pencil having a bipolar electrode is designed for use with a monopolar ESU device in a bipolar function for cutting and coagulation in medical procedures. When used with a monopolar ESU device, the ESU pencil having a bipolar electrode can also be used for monopolar application wherein a separate electrode is applied to a part of the patient's body, usually on the patient's leg, to function as the return electrode. This monopolar function is prevalent in the prior art.

The present invention also relates to a telescopic laparoscopic monopolar/bipolar ESU pencil having an adjustable length electrode capable of accommodating different depths and/or different sizes of adult and children. The telescopic laparoscopic monopolar/bipolar ESU pencil can also be used with an integrated smoke evacuator system such as that previously described in U.S. Pat. No. 5,199,944. Also, the ESU pencil of the present invention having a bipolar electrode may be combined with the suction/irrigation system and apparatus previously described in my co-pending patent application entitled "Automatic Suction/Irrigation Apparatus for Use in Laparoscopic Surgery and Electrosurgery and Method Therefor" which is being simultaneously filed with the present application and is incorporated by reference thereto. Finally, the ESU pencil of the present invention having a bipolar electrode can be combined with attachments so that it can also be used for argon beam coagulation.

BACKGROUND OF THE INVENTION

In the past, electrosurgical devices had an active electrode that was used for performing cutting and coagulation, and a return electrode which usually comprised an adhesive for attachment to a patient's skin. When the electrosurgery unit surgery pencil was activated, the RF energy circulated from the active electrode to the return electrode through the patient's body with the distances between the active and return electrodes being fairly significant.

This prior art system presents several deficiencies and creates, a number of problems that can be dangerous for the patient. First, because of the significant distance between the active and return electrodes, high voltages at high frequencies are transversed through the body in order to close the circuit between the active and return electrodes. These high voltages and frequencies can be very dangerous to the patient. Second, due to the fact that the body has an electrical resistance, the cutting and coagulation affects are significantly diminished as the distance between the active and return electrodes is increased. Accordingly, high power from the ESU is needed in order to obtain effective cutting and coagulation performance. Again, the high power required from the ESU can be dangerous to the patient.

Third, in many cases, patients have incurred significant burns because of poor contact between the return electrode and the patient's skin. Finally, dangerous capacitive coupling has occurred in laparoscopic surgery which has resulted in dangerous burns to the patient. These burns could not be detected because they are out of the field of view of the laparoscope thereby putting the patient's life in danger.

A bipolar function for open and laparoscopic procedures is presently being used with the bipolar suction of the ESU. However, this system and the related instruments are used only to stop bleeding within a patient and is not capable of performing a cutting operation.

As previously stated in the section referred to as "related application", the present invention is related to the same inventor's pending patent application entitled "Telescopic Surgical Device and Method Therefor". The similarities between the telescopic pencil described in the pending application and the present invention described in this application is that both inventions refer to a telescopic pencil which can have multifunctional applications. The main difference between the inventions is that the pending telescopic pencil patent application refers to a monopolar pencil only which has only one contact for the electrode while the ESU pencil of the present invention described in this application can be used as a monopolar instrument, a monopolar/bipolar instrument or a bipolar instrument. The ESU pencil of the present invention has an electrode which comprises two contacts, one which is used as an active electrode and another which is used as a return electrode when the instrument is used as a bipolar functioning instrument for a monopolar/bipolar functioning instrument. Alternatively, when the instrument is only used as a monopolar functioning instruments a separate electrode is applied to a different part of the patient's body, usually on the patient's leg. This separate electrode functions as the return electrode.

SUMMARY OF THE INVENTION

A principal object of the present invention an electrosurgery electrode for performing cutting and coagulation for open and closed endoscopic and laparoscopic procedures wherein the electrosurgery electrode contains both the active electrode and the return electrode on the same tip.

It is a further objection of the present invention to provide a monopolar/bipolar electrode which can be used on the monopolar section of an electrosurgery unit to perform a bipolar function thereby eliminating the need for a separate return electrode.

It is still a further object of the present invention to provide a telescopic monopolar and monopolar/bipolar electrode and pencil with smoke evacuation means wherein the distance between the operating tip of the electrode and the hand piece is adjustable to accommodate desired lengths associated with different sized patients.

It is yet a further object of the present invention to provide a telescopic monopolar and monopolar/bipolar endoscopic and laparoscopic electrode, with or without smoke evacuation means, wherein the length of the laparoscopic electrode is adjustable.

It is still a further objection of the present invention to provide a telescopic monopolar and monopolar/bipolar ESU pencil with suction/irrigation means wherein the bipolar electrode is automatically retracted upon activation of the suctioning means.

It is still a further object of the present invention to provide a telescopic monopolar and monopolar/bipolar electrode and pencil for open and closed endoscopic and laparoscopic procedures with suction/irrigation means wherein the electrode can be automatically retracted upon the activation of the suctioning means.

It is yet a further object of the present invention to provide a multi-functional telescopic ESU pencil that can be used for open and laparoscopic electrosurgery that is also capable of performing suction and irrigation, and for argon beam coagulation when used with respective attachments as previously described in reference to my pending U.S. Patent Application entitled "Telescopic Surgical Device and Method Therefor".

Accordingly, the multi-functional telescopic monopolar/bipolar surgical device of the present invention includes a bipolar electrode and a hand piece having electrical contacts wherein the bipolar electrode is connected to the electrical contacts of the hand piece and the electrical contacts of the hand piece are connected to an energy source for activating the device. An electrosurgery unit may be used as the energy source. The bipolar electrode includes an active electrode, a return electrode and an insulator which is sandwiched between the active and return electrodes. The multi-functional telescopic monopolar/bipolar surgical device may further include a telescopic member coupled to the bipolar electrode and the hand piece for adjusting the length of the bipolar electrode. Further, the multi-functional telescopic monopolar/bipolar surgical device may include a smoke evacuation means coupled to the bipolar electrode for removing smoke and other debris that is produced during electrosurgery.

The present invention is also directed to a telescopic suction/irrigation apparatus for open and endoscopic laparoscopic procedures which includes a hollow hand piece member having an open distal end and an open proximal end and connection means for connecting the hand piece to an energy source for activating suction and irrigation, an elongated hollow tubular member having distal and proximal open ends wherein the distal open end is introduced into the open proximal end of the hand piece so that the elongated hollow tubular members are concentrically contained within the channel of the hand piece, and locking means for locking the elongated hollow tubular member within the hand piece. Another embodiment of the telescopic suction/irrigation apparatus comprises a hand piece member having connection means to an energy source and means for effectuating suction and irrigation functions, a double channel telescopic suction/irrigation tube having an inner channel and outer channel wherein the double channel telescopic suction/irrigation tube is introduced into the hand piece member such that a portion of the double channel telescopic suction/irrigation tube is concentrically retained within the hand piece, connection means for connecting the inner channel of said double channel telescopic suction/irrigation tube with an irrigation port and the outer channel of the double channeled telescopic suction/irrigation tube with a suctioning port, and locking means for locking the double channel telescopic suction/irrigation tube within the hand piece member.

The present invention is also directed to a method for performing electrosurgery on a patient which comprises the steps of connecting a bipolar electrode having an active electrode and a return electrode to a hand piece with means for alternately effectuating cutting and coagulation with the bipolar electrode, connecting both the active and return electrodes to an energy source, and activating either the cutting or coagulation function using the bipolar electrode.

The foregoing and other objections, features and advantages of the present invention, as well as details of the preferred embodiments thereof, will be more fully understood from the following descriptions made in conjunction with the accompanying drawings.

DETAILED DESCRIPTION

Figure 1A:
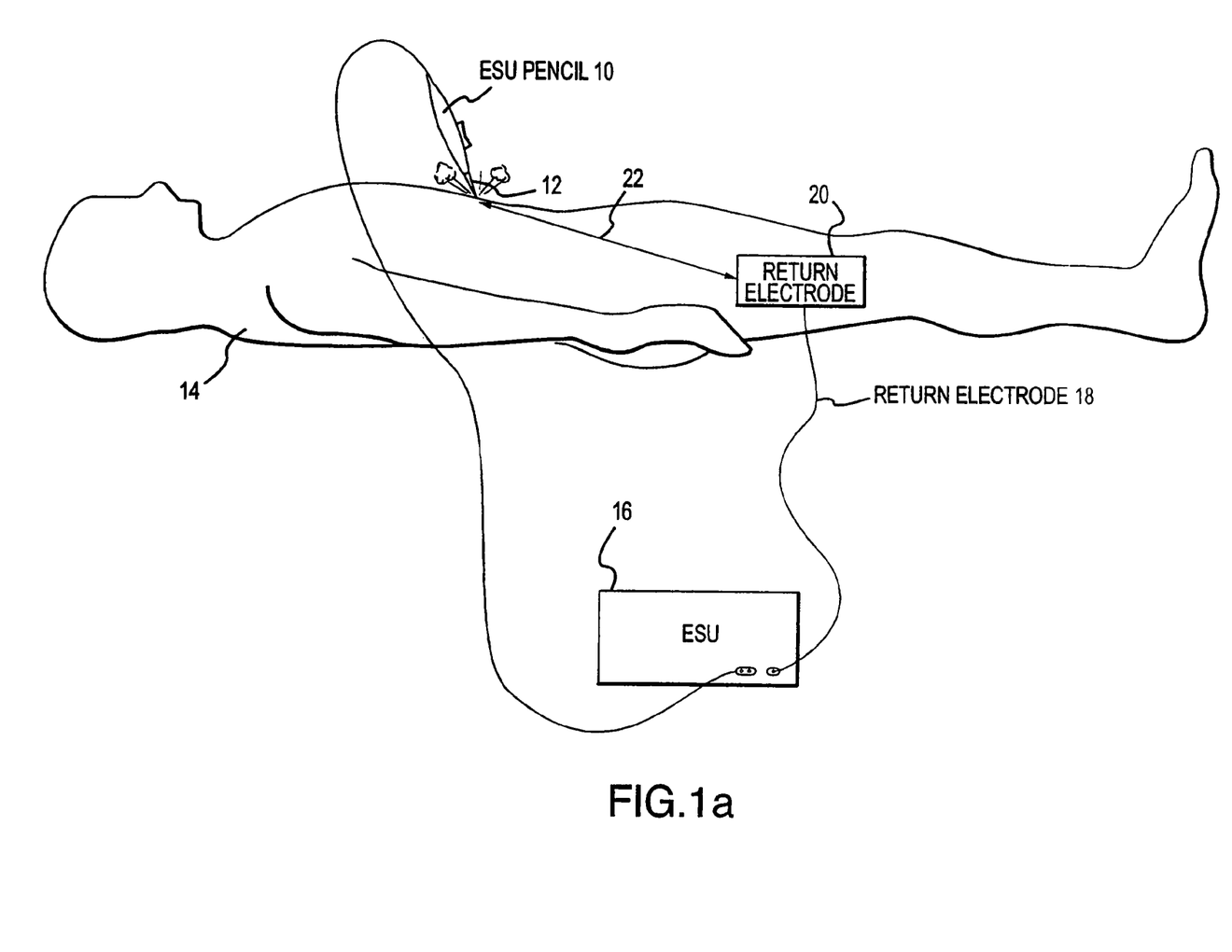
FIG. 1a is a diagrammatic view of electrosurgery being performed on a patient using a prior art ESU pencil having a monopolar electrode which requires a separate return electrode.

The present system for performing electrosurgery with an ESU pencil having a monopolar electrode is shown in FIG. 1a. The electrosurgery pencil 10 comprises an active electrode 12 which performs cutting or coagulation on a patient 14. The ESU pencil 10 comprising active electrode 12 is connected to the electrosurgery unit 16 which provides the energy source to activate the ESU pencil 10. A return electrode 18 comprises an adhesive patch 20 which is positioned and applied to the patient 14 at a considerable distance 22 away from the active electrode 12. The return electrode 18 is also connected to the electrosurgery unit 16 thereby creating a close circuit wherein the voltage and frequency emitted from the active electrode 12 is transmitted through the body of the patient 14 and received by return electrode 20. FIG. 1a illustrates how monopolar electrosurgery is presently performed.

Figure 1B:
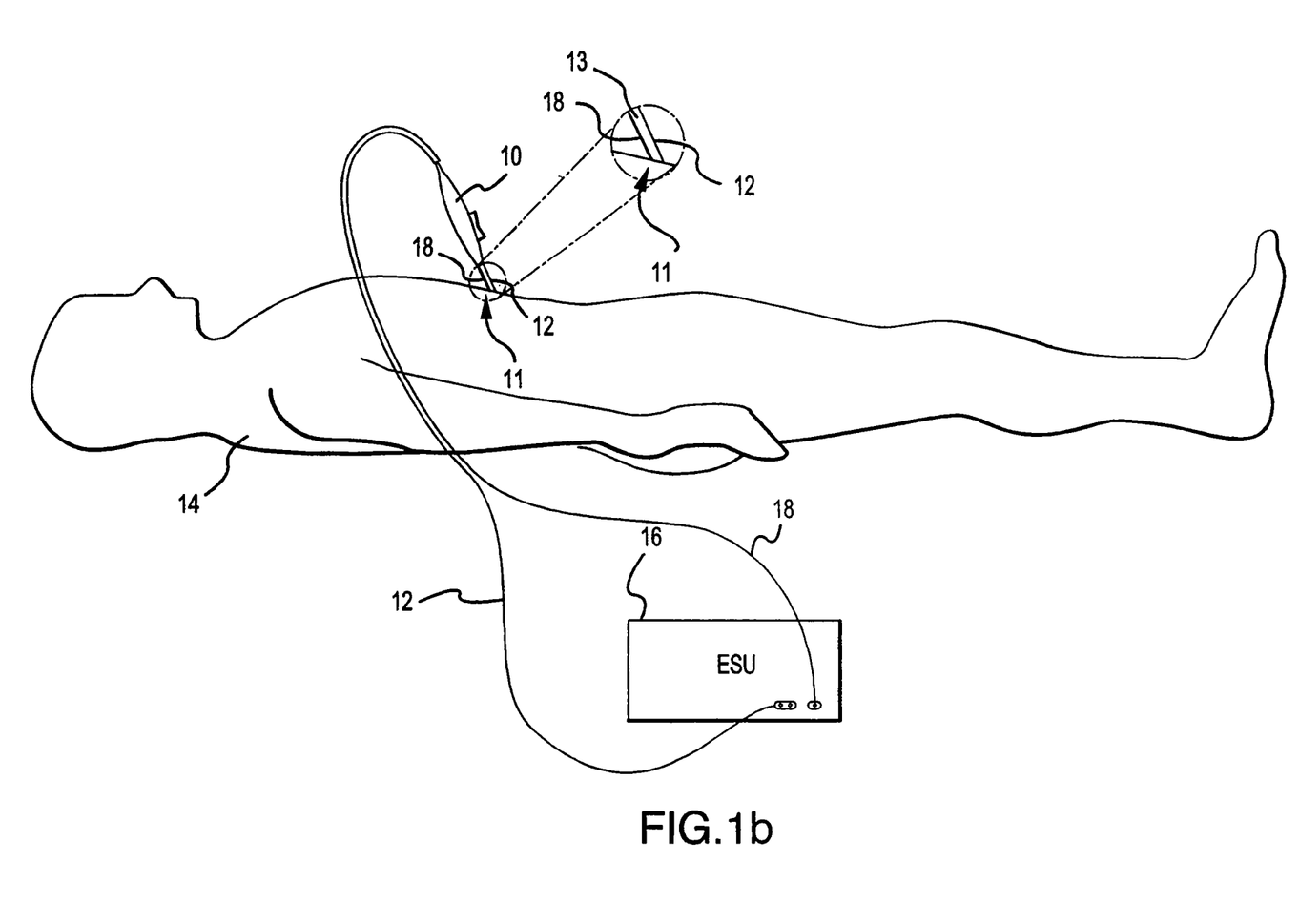
FIG. 1b is a diagrammatic view of electrosurgery being performed on a patient using the telescopic monopolar/bipolar surgical device of the present invention for electrosurgery.

Electrosurgery performed on a patient using the multifunctional telescopic monopolar/bipolar surgical device of the present invention is shown in FIG. 1b. With the present invention, the electrosurgery pencil 10 comprises a bipolar electrode 11 which comprises an active electrode 12 and a return electrode 18 which are separated by a material dielectric 13 which functions as an insulator. Both the active electrode 12 and the return electrode 18 are connected to the electrosurgery unit 16 thereby performing a completed circuit. When the electrosurgery unit 16 is activated and the bipolar electrode 11 touches the tissue of the patient 14, the circuit is closed through a very small portion of the patient's tissue between the active electrode 12 and the return electrode 18. This shortened distance between the active electrode 12 and return electrode 18 results in decrease of the power requirement from that previously needed in association with the monopolar electrode of the prior art in order to effectuate cutting and coagulation. This decreased distance between the two electrodes 12, 18 also results in decreasing the dangers associated with passing high voltages at high frequencies throughout a substantial portion of the patient's body, one of those risks being an increased possibility of burns to the patient.

Figure 2A:
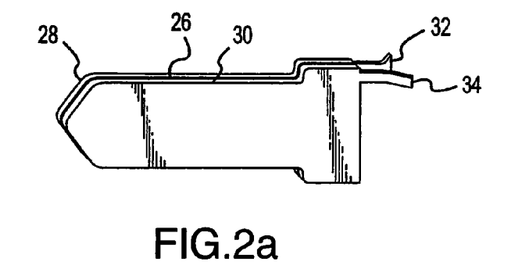
FIG. 2a is a perspective view of a first embodiment of a bipolar electrode for use within the telescopic monopolar/bipolar surgical device of the present invention for electrosurgery which can also function as a monopolar electrode.
Figure 2B:
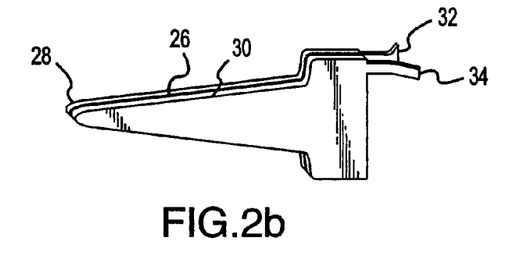
FIG. 2b is a perspective view of a second embodiment of a bipolar electrode for use within the telescopic monopolar/bipolar surgical device of the present invention for electrosurgery which can also function as a monopolar electrode.
Figure 2C:
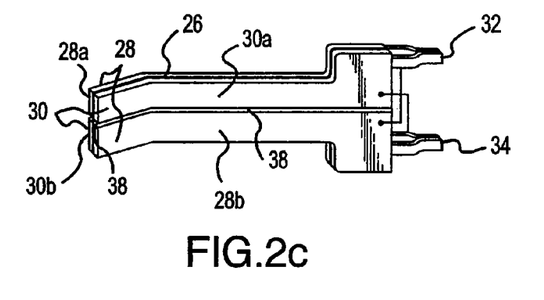
FIG. 2c is a perspective view of a third embodiment of a bipolar electrode for use within the telescopic monopolar/bipolar surgical device of the present invention for electrosurgery which can also function as a monopolar electrode.

FIGS. 2a-c show perspective views of different embodiments of bipolar electrodes which comprise part of the multifunctional telescopic monopolar/bipolar surgical device of the present invention for open electrosurgery procedures. These electrodes are capable of exhibiting both bipolar and monopolar functioning in conjunction with an electrosurgery unit.

FIG. 2a represents a perspective view of a bipolar blade electrode. An insulator 26 is sandwiched between the active electrode 28 and the return electrode 30. Active electrode 28 further comprises an active prong 32 which is designed to come in contact with an active conductor contained within the telescopic element of the device of the present invention which is shown and described later with reference to FIGS. 3b and 3c. Further, the return electrode 30 comprises a return prong 34 which is designed to make contact with a return conductor contained within the telescopic element of the device of the present invention which is also shown and described later with reference to FIGS. 3b-3c.

FIG. 2b represents a perspective view of a bipolar needle electrode. Again, an insulator 26 is sandwiched between the active electrode 28 and the return electrode 30 wherein the active electrode 28 and return electrode 30 further comprise an active prong 32 and return prong 34, respectively, for connection to conductor elements contained within a telescopic element of a device of the present invention as shown in FIGS. 3b-3c.

FIG. 2c represents a perspective view of a special angled bipolar electrode that can be used for cutting and/or coagulation, as well as for surface coagulation or ablation. An insulator 26 is sandwiched between active and return electrodes wherein one of each of an active electrode 28 and a return electrode 30 are positioned on opposite sides of the insulator 26. More specifically, on a first side (not shown) of insulator 26 there is a top active electrode 28A and a bottom return electrode 30B and on a second side 38 of insulator 26 there is a top return electrode 30A and a bottom active electrode 28B. Active prong 32 connects top active electrode 28A to bottom active electrode 28B while return prong 34 serves to connect top return electrode 30A to bottom return electrode 30B thereby forming connection means for the active electrode 28 and return electrode 30, respectively, when connecting the active and return electrodes 28, 30 to conductors contained within the telescopic elements of the device of the present invention as further explained with reference to FIGS. 3b-3c. The previously described electrodes may further vary by comprising a variety of different shapes without detracting from the purpose of the invention.

Figure 2D:
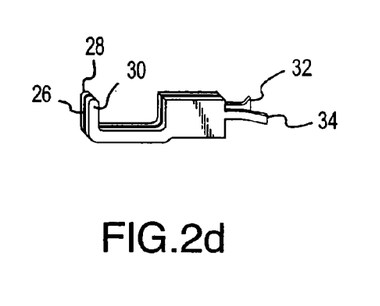
FIG. 2d is a perspective of a first embodiment of a bipolar electrode used in the multifunctional telescopic monopolar/bipolar surgical device of the present invention for endoscopic and/or laparoscopic procedures wherein the bipolar electrode is capable of a monopolar function.
Figure 2E:
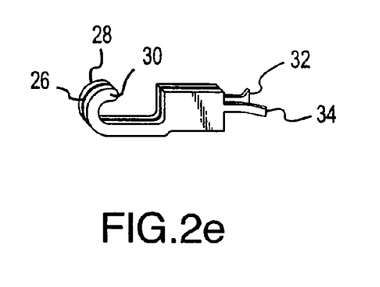
FIG. 2e is a perspective view of a second embodiment of a bipolar electrode used in the multifunctional telescopic monopolar/bipolar surgical device of the present invention for endoscopic and/or laparoscopic procedures wherein the bipolar electrode is capable of a monopolar function.
Figure 2F:
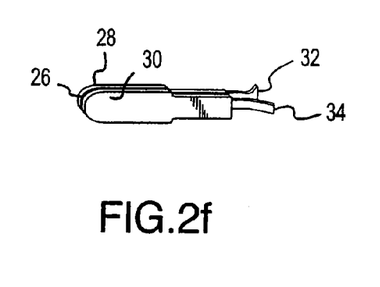
FIG. 2f is a perspective view of a third embodiment of a bipolar electrode used in the multifunctional telescopic monopolar/bipolar surgical device of the present invention for endoscopic and/or laparoscopic procedures wherein the bipolar electrode is capable of a monopolar function.

FIGS. 2d-2f depict perspective views of bipolar electrodes which comprise part of the multifunctional telescopic monopolar/bipolar surgical device of the present invention for performing endoscopic and/or laparoscopic procedures wherein the electrode is also capable of monopolar functioning alone. FIGS. 2d and 2e represent hook-shaped bipolar electrodes for use in endoscopic and laparoscopic procedures wherein the bipolar electrodes are also capable of functioning as monopolar electrodes. FIG. 2f shows a paddle-shaped bipolar electrode for use in endoscopic and/or laparoscopic procedures which may also function as a monopolar electrode. All of the bipolar electrodes depicted in FIGS. 2d-2f comprise an insulator 26 which is sandwiched between an active electrode 28 and a return electrode 30. Further, the active electrode 28 comprises an active prong 32 while the return electrode 30 comprises a return prong 34 wherein both the active prong 32 and return prong 34 serve as connection means for connecting the active electrode 28 and return electrode 30 to conductors contained within a laparoscopic/endoscopic telescope element of the device of the present invention as further detailed in reference to FIG. 3d.

Other electrode shapes and forms may be used with respect to the bipolar electrodes for endoscopic and/or laparoscopic procedures without detracting from the purpose of the invention. Further, the active electrode 28 and return electrode 30 on all of the previously described bipolar electrodes in reference to FIGS. 2a-2f may be reversed such that the active electrode 28 and return electrode 30 are on opposite sides of the insulator 26 than those on which they are depicted in the Figures.

Active electrode 28 is preferably comprised of stainless steel or other suitable conductors and return electrode 30 is preferably comprised of a ceramic or other suitable material which can function as an insulator. The insulator 26 is preferably comprised of a dielectric material which is suitable for use as a dielectric in radio frequency applications and at very high temperatures such as certain types of ceramics. However, any dielectric materials that can meet the conditions for RF applications at very high temperatures may be used.

As previously explained with reference to FIG. 1B, the circuit created by the active electrode 28 and return electrode 30 is closed when the ESU is activated and the electrode touches the tissue of a patient. This very small portion of the patient's tissue closes the gap between the active electrode 28 and the return electrode 30. As a result, much less power is needed to traverse the patient's tissue in order to close the circuit and effectuate the cutting and coagulation operations. A load resistor can be installed in series to avoid an accidental short circuit in between the two electrodes.

Figure 3A:
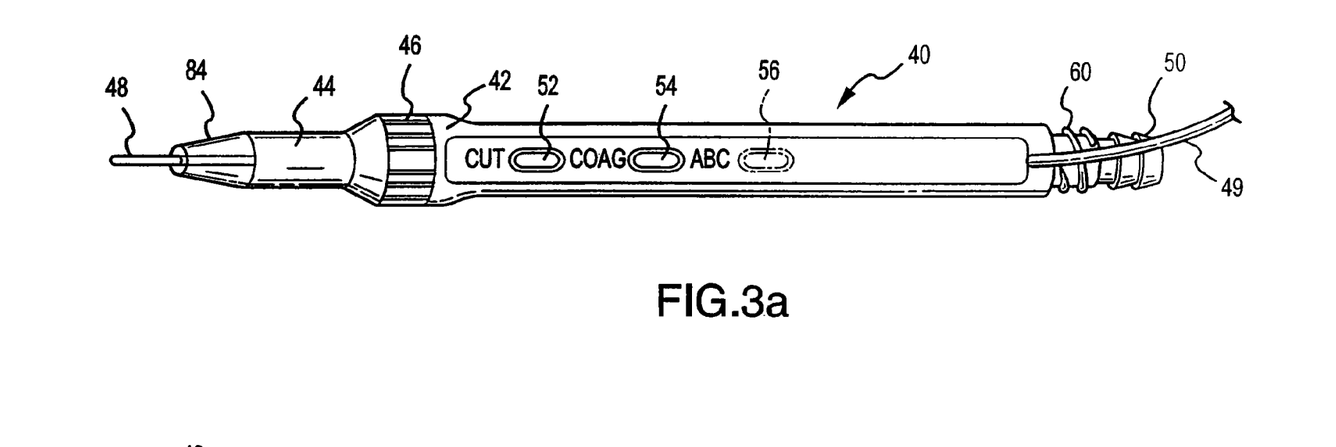
FIG. 3a is a perspective view of the multi-functional monopolar/bipolar telescopic electrosurgical device of the present invention.
Figure 3B:
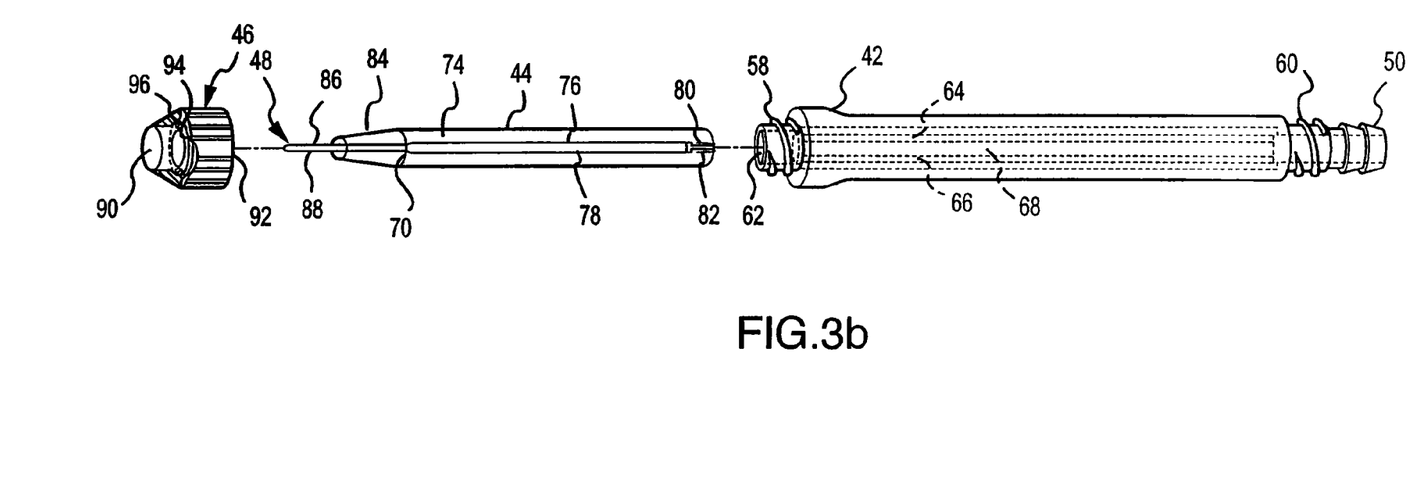
FIG. 3b is a perspective exploded view of the device in FIG. 1 shown without the electrical cord.
Figure 3C:
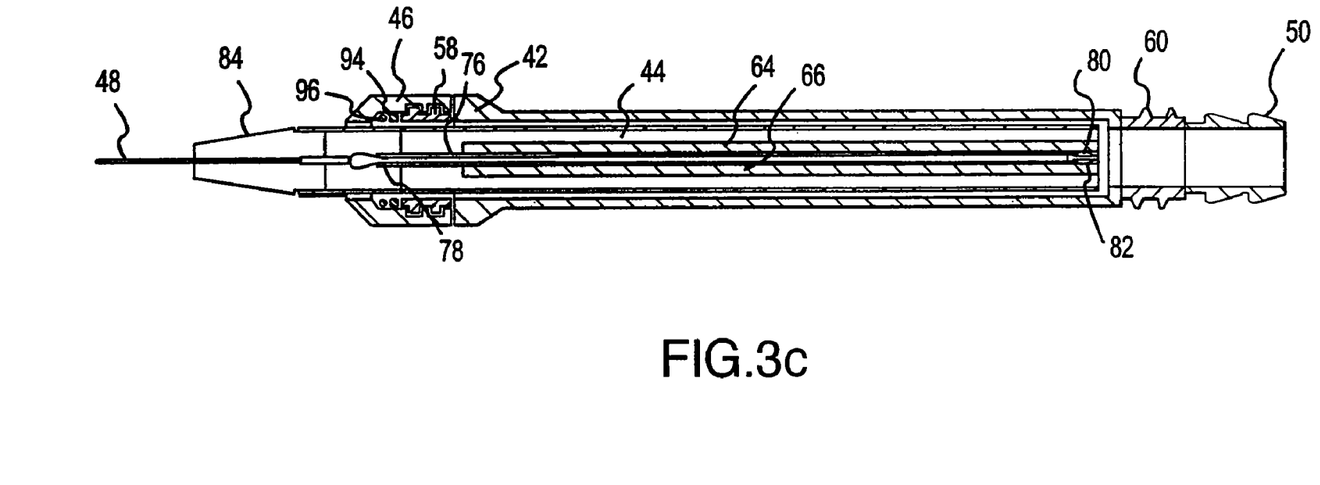
FIG. 3c is cross-sectional view of the device in FIG. 3A shown without the electrical cord.

Turning now to FIG. 3a, there is shown a perspective view of the multi-functional telescopic monopolar/bipolar electrosurgical device of the present invention. In brief, the multifunctional telescopic monopolar/bipolar electrosurgical device 40 of the present invention comprises a main body 42, a telescopic body 44 circumferentially contained within the main body 42 such that it can be extended outward from, and retracted into, the main body 42, a locking element 46 which locks the telescopic body 44 to the main body 42 at a predetermined extracted length, a bipolar electrode 48 contained within the telescopic body and main body such that it is capable of being in electrical contact with an electrosurgery unit, and a connector element 50 for connecting the main body 42 of the device 40 to a smoke evacuator tubing (not shown). The main body 42 of the device 40 further comprises a series of selection buttons, one selection button for cutting 52, one selection button for coagulation 54, and one selection button for argon beam coagulation 56. The selection button for argon beam coagulation is optional. The main body may be provided with only cutting and coagulation selection buttons 52, 54.

An exploded view of the multifunctional telescopic monopolar/bipolar electrosurgical device 40 of the present invention is illustrated in FIG. 3b. The main body 42 of the device 40 comprises a distal thread 58 and a proximal thread 60 which are connected by a channel 62. The main body 42 further comprises an active contact 64 and a return contact 66 which are located parallel to one another on an interior surface of the channel 62 having a gap located there between which resembles an elongated slot 68. The telescopic body 44 comprises a distal end 70 and a proximal end 72 which are separated by a second channel 74 that is smaller in diameter than the channel 62 contained within the main body 42. The telescopic body 44 further comprises a pair of elongated conductors 76, 78 located within the second channel 74 of the telescopic body 44. Each of the elongated conductors 76, 78 terminate in contact prongs 80, 82, respectively, such that the contact prongs 80, 82 are located on the external surface of the telescopic body 44 near its proximal end 72. A hollow nozzle 84 may be connected to the distal end 70 of the telescopic body 44.

The bipolar electrode 48 is connected to the telescopic body 44 such that the active electrode 86 and return electrode 88 are in contact with the elongated conductors 76, 78, respectively. Finally, the locking element 46 comprises a hollow interior having a distal end 90 and a proximal end 92. The locking element 46 further comprises a ridge 94 contained within its hollow interior and an "O" ring 96 which is seated on the ridge 94. As a result, the locking element 46 can be slid over the telescopic body 44 and connected to the distal thread 58 of the main body 42 to enable the telescopic body 44 to be locked in position within the main body 42.

FIG. 3c shows a cross sectional view of the multifunctional telescopic monopolar/bipolar electrosurgery unit pencil shown in FIG. 3a. As previously described, the main body 42 contains active contact 64 and patient return contact 66 which are parallel to one another so that they are separated by the same distance along their entire lengths. Contact prongs 80, 82 contained on the external surface of the telescopic body 44 are slightably engaged and maintained within the elongated slot 68 which separates the active contact 64 from the patient return contact 66. The bipolar electrode 48 is connected to the contact prongs 80, 82 via the elongated conductors 76, 78. The telescopic body 44 is extracted or retracted within the main body 42 to adjust for the desired length of the bipolar electrode 48.

Argon beam coagulation attachments (not shown) replace the telescopic body 44 described above with a special telescope and end attachment similar to those described in my previous patent application entitled "A Telescopic Surgical Device and Method Therefor" may be attached to the proximal thread 60 of the main body 42 of the device 40. A suction/irrigation attachment such as that later described and shown in FIGS. 4a-4b, as well as a connector for smoke evacuation tubing (not shown) may also be connected to proximal thread 60 of the main body 42 of the device 40. The locking element 46 is threaded onto the distal thread 58 of the main body 42 of the device 40 in order to lock the telescopic body 44 in place. The telescopic body 44 is locked in position by tightening the locking element 46 against the distal thread 58 of the main body 42. As a result, the ridge 94 contained within the locking element 46 is pushed forward such that it presses over the "O" ring 96 which in turn presses over the telescopic body 44 thereby locking it in place.

During use, when either the cutting button 52 or the coagulation button 54 is depressed, the active contact 64 is energized and the return contact 66 acts to return current from the patient to the electrosurgery unit. Contact prongs 80, 82 function to pass the radio frequency energy through elongated conductor 76 to the bipolar electrode 48 and then return the RF energy through elongated conductor 78 back to contact prong 82. If the multifunctional telescopic monopolar/bipolar surgical pencil device of the present invention is used for monopolar only, then the active contact 64 and return contact 66 will both conduct the active energy and a separate return electrode will be provided and utilized as represented in FIG. 1A. Energy is brought to the multifunctional telescopic monopolar/bipolar surgical pencil device of the present invention by electrical cord 49 (See FIG. 3a) which is connected to an electrosurgery unit (not shown).

Figure 3D:
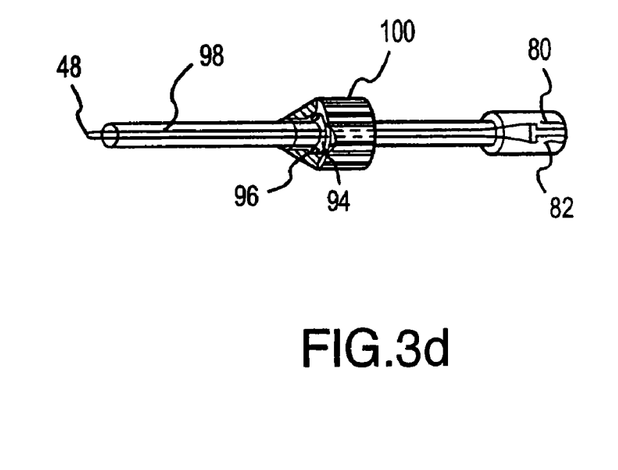
FIG. 3d is perspective view of an endoscopic and/or laparoscopic telescope element which can replace the telescopic element of the multi-functional monopolar/bipolar telescopic electrosurgical device shown in FIG. 3C to create a multi-functional monopolar/bipolar telescopic electrosurgical device for endoscopic and/or laparoscopic procedures.

Turning now to FIG. 3d, there is shown an endoscopic/laparoscopic telescopic body 98 which replaces the telescopic body 44 shown in FIGS. 3b-3c in order to perform endoscopic and/or laparoscopic procedures. The second locking element 100 works similar to the locking element 46 described with reference to FIGS. 3b-3c. The cutting operation is activated when the cutting button 52 is depressed and coagulation is activated when the coagulation button 54 is depressed. Argon beam coagulation button number 56 is optional and, if used, the endoscopic/laparoscopic telescope body 98 is replaced with a different telescope such as that described in my pending patent application entitled "A Telescopic Surgical Device and Method Therefor" and an adaptor is attached to the end of the device 40 at the proximal thread 60 of the main body 42 of the device 40. The adaptor is very similar to the adaptor for suction/irrigation that is later shown and described with reference to FIG. 4.

Figures 4A, 4B, 4C, 4D:
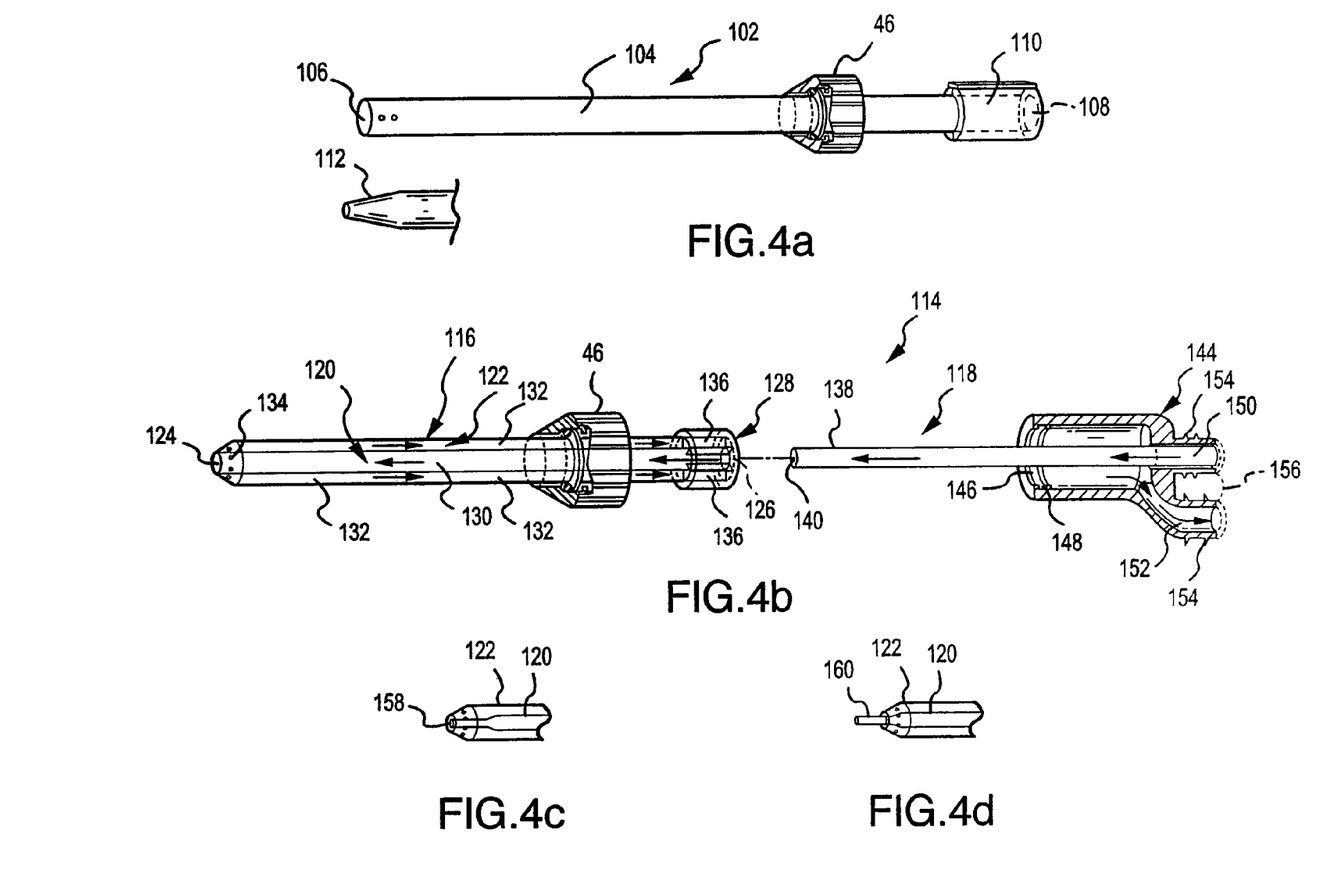
FIG. 4a is a perspective view of a suction/irrigation telescope which can replace the electrosurgery telescope in FIG. 3C or the laparoscopic telescope in FIG. 3D to provide a telescopic surgical device with suction/irrigation means capable of performing either suction or irrigation.
FIG. 4b is a perspective exploded view and partial cross-sectional view of a second embodiment of a suction/irrigation telescope which can replace the electrosurgery telescope in FIG. 3C or the laparoscopic telescope in FIG. 3D to provide a telescopic device with suction/irrigation means capable of performing suction and irrigation simultaneously.
FIG. 4c is a partial cross sectional view of a hydro dissection nozzle wherein the internal tube of the nozzle is shown retracted.
FIG. 4d is a partial cross sectional view of the hydro dissection nozzle shown in FIG. 4c with the internal tube shown extended.
Figure 5:
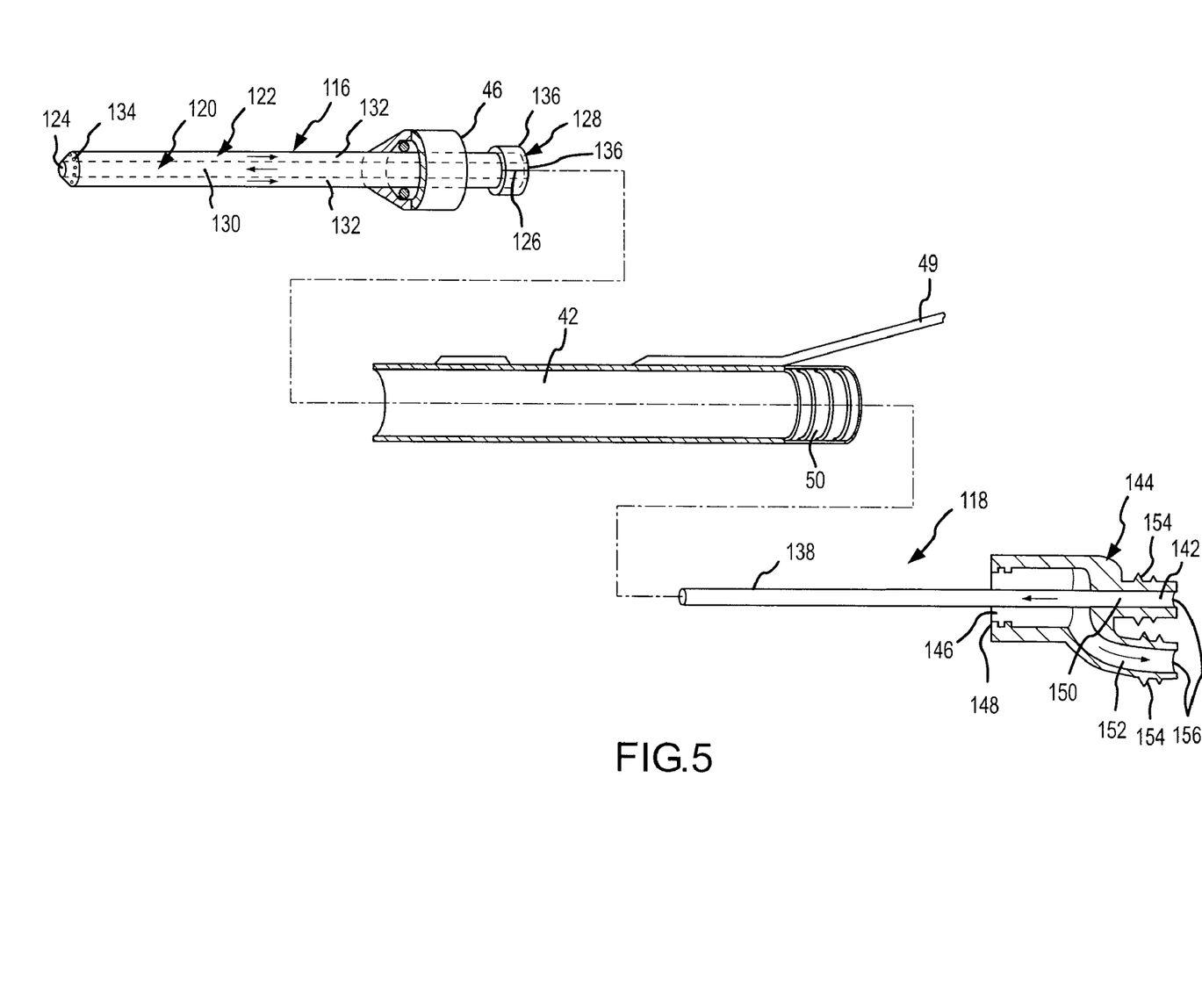
FIG. 5 is a perspective exploded view of one embodiment of the telescopic suction/irrigation apparatus of the present invention.

FIGS. 4a-4c show another embodiment of the electrosurgery pencil of the present invention which is directed toward a telescopic suction/irrigation pencil for electrosurgery. The telescopic monopolar/bipolar surgical pencil depicted and described in FIGS. 3a-3d will become a telescopic suction/irrigation pencil by replacing the telescopic body 44 in FIGS. 3b-3c and the endoscopic/laparoscopic telescopic body 98 in FIG. 3d with the attachments presented in FIGS. 4a-4b. The resulting telescopic suction/irrigation pencil is advantageous in that it permits the surgeon to adjust the lengths of the suction/irrigation tip without the need for removing and reattaching tips of different lengths.

FIG. 4a shows a perspective view of a first embodiment of a suction/irrigation attachment 102 comprising a singular hollow tube 104 having a distal end 106 and a proximal end 108. The suction/irrigation attachment 102 further comprises a sliding guide 110 which is circumferentially fit about the proximal end 108 of the singular hollow tube 104 thereby allowing the suction/irrigation attachment 102 to be slidably engaged within the main body 42 of the telescopic monopolar/bipolar electrosurgery device 40 shown in FIG. 3b. The locking element 46 shown in FIG. 3b is also used in conjunction with the suction/irrigation attachment 102 shown in FIG. 4a in order to lock the suction/irrigation attachment 102 in place at a predetermined extracted length from the main body 42 shown in FIG. 3b. The resulting device is a telescopic suction/irrigation pencil for use with electrosurgery as well as laparoscopic and endoscopic procedures.

Suction and irrigation are activated by using the cutting button 52 shown in FIG. 3a for irrigation and the coagulation button 54 shown in FIG. 3a for suction. During irrigation, the irrigation fluid enters the telescopic suction/irrigation pencil through connector element 50, then passes through the proximal end 108 of the singular hollow tube 104 shown in FIG. 4a and then exits the telescopic suction/irrigation pencil through the distal end 106 of the singular hollow tube 104 shown in FIG. 4a. In contrast, when suction is activated, fluid is drawn from the patient and enters the telescopic suction/irrigation pencil at the distal end 106 of the singular hollow tube 104, is further drawn past the proximal end 108 of the singular hollow tube 104, and finally exits the telescopic suction/irrigation pencil through the connector element 50 shown in FIG. 3b.

The distal end 106 of the suction/irrigation attachment 102 may be narrowed to form a nozzle 112 such as that shown in FIG. 4a. The nozzle 112 configuration of the distal end 106 facilitates the use of the telescopic suction/irrigation pencil for hydra-dissection by enabling the irrigation fluid to exit the distal end 106 of the suction/irrigation attachment 102 with high pressure and velocity.

FIG. 4b illustrates an exploded perspective view of a second embodiment of a suction/irrigation attachment 114 which is capable of performing suction and irrigation simultaneously. The lengths of the telescopic suction and irrigation tubes may also be adjusted. The second embodiment of the suction/irrigation attachment 114 comprises a double channeled tube 116 and a singular connection tube 118. The double channeled tube 116 comprises a first hollow tube 120 circumferentially contained within a second hollow tube 122 wherein the first and second hollow tubes 120, 122 are of substantially the same length. The double channeled tube 116 further includes a distal end 124, a proximal end 126, a spacer element 128 located at the proximal end 126 of the double channeled tube 116, and a locking element 46 which functions like the locking element 46 shown and described with reference to FIG. 3b.

The double channeled tube 116 contains a central inner channel 130 which is defined by the hollow inner area of the first hollow tube 120 and an outer ring-shaped channel 132 which is defined by the opening generated by the difference between the inner diameter of the second hollow tube 122 and the outer diameter of the inner hollow tube 120. Irrigation is conducted through the central inner channel 130 while suction is conducted through the outer ring-shaped channel 132.

The second hollow tube 122 is closed about the first hollow tube 120 at the distal end 124 of the double channeled tube 116 but a plurality of apertures 134 are contained about the circumference of the second hollow tube 122 near distal end 124 thereby creating an opening through which fluid can pass through the outer ring-shaped channel 132. The spacer element 128 comprises a shortened hollow cylinder having a proximal open end and a plurality of wings 136 located within its opposite open end. The plurality of wings 136 are positioned within the outer ring-shaped channel 132 located between the first hollow tube 120 and the second hollow tube 122 to maintain the distance between the tubes 120, 122 and support the outer ring-shaped channel 132 while still allowing irrigation fluid to pass through the outer ring-shaped channel 132 with minimal resistance.

The singular connection tube 118 comprises a tube 138 having an open distal end 140 and an open proximal end 142 wherein the open proximal end 142 is seated within a multi-connector piece 144. Multi-connector piece 144 comprises a hollow piece having a large open distal end 146 with grooves 148 for receiving threads and two smaller channels 150, 152 each having threads 154 located at its proximal end 156. Threaded channel 150 is designed to be attached to an irrigation means while threaded channel 152 is designed for attachment to a suctioning means.

During use, the grooves 148 at the large open distal end 146 of the multi-connector piece 144 are connected to the proximal thread 60 of the main body 42 of the device 40 shown in FIG. 3b while the tube 138 is inserted through the channel 62 of the main body 42 such that tube 138 will exit the channel 62 and enter the central inner channel 130 of the first hollow tube 120 of the double channeled tube 116 when the spacer element 128 is slid within the main body 42 of the device 40 shown in FIG. 3b. Tube 138 has an outer diameter that is slightly smaller than the inner diameter of the first hollow tube 120 so that hollow tube 120 and tube 138 form a telescope when concentrically enjoined.

When irrigation is activated, irrigation fluid will be introduced under pressure through the open proximal end 142 of tube 138 and will traverse the telescopic configuration resulting from joining tube 138 inside of first hollow tube 120, and will then exit at the distal end 124 of the double channeled tube 116 through the first hollow tube 120. When suction is activated, suctioning means is applied at suctioning channel 152 and fluid is drawn from the patient through the plurality of apertures 134 contained within the second hollow tube 122. The fluid is drawn through the ring-shaped outer channel 132 and then exits at the suctioning channel 152. Spacer element 128 slides within the main body 42 of the device 40 shown in FIG. 3b and the second hollow tube 122 is locked into place by connecting locking element 46 to distal thread 58 of the main body 42 of the device 40.

The distal end 124 of the double channeled tube 116 of the suction/irrigation attachment shown in FIG. 4b may comprise an alternative configuration such as that shown in FIGS.

4c-4d. FIGS. 4c-4d depict a nozzle configuration in which the distal open end 158 of first hollow tube 120 forms a needle nose 160 which is capable of being extracted and retracted from within the second hollow tube 122 thereby allowing the operator or surgeon to adjust the length of the irrigation means such that it extends beyond the length of the suctioning means at the cite of application.

While the invention has been particularly shown and described with reference to the preferred embodiments thereof, it will be understood by those skilled in the art that changes in form and detail of the foregoing may be made without departing from the spirit and scope of the present invention. For example, if a different shape or form is given to the monopolar/bipolar electrodes but they are still capable of functioning with a monopolar ESU suction to provide a bipolar function, this new configuration is believed to be included within the scope of the present invention. Further, different locking means for locking the telescopic functioning elements in place as well as different configurations for providing electrical contact means within the telescopic body and main body of the device are believed to be included within the spirit and scope of the present invention.

The invention claimed is:

1. A multifunctional electrosurgery pencil for use with an energy source comprising:
    an electrode;
    a handpiece with means for connecting said electrode to said energy source;
    telescopic member means contained within said handpiece for adjusting the length of said telescopic member means extending from said handpiece wherein at least a portion of said electrode is contained within said telescopic member means; and
    smoke evacuation means coupled to said handpiece for removing smoke and debris produced during a medical procedure using said electrosurgery pencil and energy source.

2. The multifunctional electrosurgery pencil of claim 1 wherein said energy source is an electrosurgery unit.

3. The multifunctional electrosurgery pencil of claim 1 further comprising means for effectuating at least one of alternate and simultaneous suction and irrigation functions.

4. The multifunctional electrosurgery pencil of claim 3 wherein said energy source is an electrosurgery unit.

5. The multifunctional electrosurgery pencil of claim 1 wherein said electrode is a bipolar electrode.

6. A multifunctional telescopic electrosurgery pencil for use with an energy source comprising:
    a main body having a first end and a second end in continuous communication with one another wherein the second end is capable of being coupled to smoke evacuation means for removing smoke and debris produced during a medical procedure using said electrosurgery pencil and energy source;
    a movable telescopic body circumferentially contained within the first end of the main body; and
    an electrode contained within at least a portion of the movable telescopic body such that it is capable of being in electrical contact with the energy source.

7. The multifunctional telescopic electrosurgery pencil of claim 6 wherein said energy source is an electrosurgery unit.

8. The multifunctional telescopic electrosurgery pencil of claim 6 further comprising means for effectuating at least one of alternate and simultaneous suction and irrigation functions.

9. The multifunctional telescopic electrosurgery pencil of claim 8 wherein said energy source is an electrosurgery unit.

10. The multifunctional telescopic electrosurgery pencil of claim 6 wherein said electrode is a bipolar electrode.

* * * * *